US008038994B2

(12) United States Patent
Schultes et al.

(10) Patent No.: US 8,038,994 B2
(45) Date of Patent: Oct. 18, 2011

(54) COMBINATION THERAPY FOR TREATING DISEASE

(75) Inventors: Birgit C. Schultes, Arlington, MA (US); Christopher F. Nicodemus, Charlestown, MA (US); Antoine A. Noujaim, Edmonton (CA); Ragupathy Madiyalakan, Edmonton (CA)

(73) Assignee: Quest Pharmatech Inc. (CA)

( * ) Notice: Subject to any disclaimer, the term of this patent is extended or adjusted under 35 U.S.C. 154(b) by 1783 days.

(21) Appl. No.: 10/831,886

(22) Filed: Apr. 26, 2004

(65) Prior Publication Data
US 2005/0063976 A1   Mar. 24, 2005

Related U.S. Application Data

(63) Continuation-in-part of application No. 09/871,339, filed on May 31, 2001, now abandoned, which is a continuation of application No. 08/913,290, filed as application No. PCT/IB96/00461 on May 15, 1996, now Pat. No. 6,241,985, and a continuation-in-part of application No. PCT/IB02/05794, filed on Oct. 28, 2002.

(60) Provisional application No. 60/339,240, filed on Oct. 26, 2001.

(51) Int. Cl.
A61K 39/395 (2006.01)

(52) U.S. Cl. .............. 424/138.1; 424/141.1; 424/156.1

(58) Field of Classification Search .......................... None
See application file for complete search history.

(56) References Cited

U.S. PATENT DOCUMENTS

| | | | |
|---|---|---|---|
| 3,865,689 A | 2/1975 | Goldenberg | |
| 4,331,647 A | 5/1982 | Goldenberg | |
| 4,348,376 A * | 9/1982 | Goldenberg | 424/1.49 |
| 4,471,057 A | 9/1984 | Koprowski et al. | |
| 4,740,371 A | 4/1988 | St. Remy et al. | |
| 4,879,225 A | 11/1989 | Morgan, Jr. et al. | |
| 4,940,670 A | 7/1990 | Rhodes | |
| 4,950,480 A | 8/1990 | Barber et al. | |
| 4,975,278 A * | 12/1990 | Senter et al. | 424/178.1 |
| 4,997,762 A | 3/1991 | Hanna, Jr. et al. | |
| 5,009,888 A | 4/1991 | Dunn | |
| 5,013,547 A | 5/1991 | Sweet et al. | |
| 5,053,224 A | 10/1991 | Koprowski et al. | |
| 5,075,218 A | 12/1991 | Jette et al. | |
| 5,165,922 A * | 11/1992 | Hellstrom et al. | 424/155.1 |
| 5,183,657 A | 2/1993 | Buurman | |
| 5,194,254 A | 3/1993 | Barber et al. | |
| 5,240,833 A | 8/1993 | Nudelman et al. | |
| 5,308,614 A | 5/1994 | Hakomori | |
| 5,389,530 A | 2/1995 | Hakomori | |
| 5,478,556 A | 12/1995 | Elliott et al. | |
| 5,500,215 A | 3/1996 | Hakomori | |
| 5,506,343 A | 4/1996 | Kufe | |
| 5,512,283 A | 4/1996 | Byers et al. | |
| 5,518,723 A | 5/1996 | Devico et al. | |
| 5,530,101 A | 6/1996 | QuEn et al. | |
| 5,532,159 A | 7/1996 | Webb et al. | |
| 5,583,202 A | 12/1996 | Zanetti | |
| 5,591,593 A | 1/1997 | Courtenay-Luck | |
| 5,652,114 A | 7/1997 | Chu et al. | |
| 5,683,674 A | 11/1997 | Taylor-Papadimitriou et al. | |
| 5,688,657 A | 11/1997 | Tsang et al. | |
| 5,725,856 A | 3/1998 | Hudziak et al. | |
| 5,726,023 A | 3/1998 | ChEver et al. | |
| 5,783,186 A * | 7/1998 | Arakawa et al. | 424/143.1 |
| 5,807,978 A | 9/1998 | Kokolus et al. | |
| 5,869,445 A | 2/1999 | Cheever et al. | |
| 5,933,439 A | 8/1999 | Hyuga et al. | |
| 5,972,347 A | 10/1999 | Eder et al. | |
| 5,976,818 A | 11/1999 | O'Brien | |
| 5,977,316 A | 11/1999 | Chatterjee et al. | |
| 5,997,869 A | 12/1999 | Goletz et al. | |
| 6,068,830 A | 5/2000 | Diamandis et al. | |
| 6,077,519 A | 6/2000 | Storkus et al. | |
| 6,080,557 A | 6/2000 | Sims et al. | |
| 6,086,873 A | 7/2000 | Sykes et al. | |
| 6,088,613 A | 7/2000 | Unger | |
| 6,096,289 A | 8/2000 | Goldenberg | |
| 6,123,939 A * | 9/2000 | Shawver et al. | 424/130.1 |
| 6,140,091 A | 10/2000 | Raso et al. | |
| 6,258,358 B1 | 7/2001 | Romet-Lemonne et al. | |

(Continued)

FOREIGN PATENT DOCUMENTS

| | | |
|---|---|---|
| EP | 0 153 871 | 9/1984 |
| EP | 0234122 | 9/1987 |
| EP | 0308208 | 3/1989 |
| EP | 315456 | 5/1989 |
| EP | 0315456 | 5/1989 |
| EP | 0288082 | 4/1998 |
| EP | 0553244 | 12/1998 |
| WO | WO 87/00053 | 1/1987 |
| WO | WO 88/03954 | 6/1988 |
| WO | WO-89/01629 | 2/1989 |

(Continued)

OTHER PUBLICATIONS

Clark (Protein Engineering of Antibody Molecules for Prophylactic and Therapeutic Applications in Man, 1993, pp. 4-5).*

(Continued)

*Primary Examiner* — Karen Canella
(74) *Attorney, Agent, or Firm* — Sheridan Ross P.C.

(57) ABSTRACT

Disclosed are methods for treating cancer comprising administering a xenotypic antibody and a chemotherapeutic drug to a patient suffering from cancer. Also disclosed is a method for inducing a host immune response in a patient against a multi-epitopic in vivo tumor antigen present in the host serum, which antigen does not elicit an effective host immune response, comprising administering to the patient a chemotherapeutic drug and a composition comprising a binding agent that specifically binds to a first epitope on the antigen and allowing the binding agent to form a binding agent/antigen pair, wherein an effective host immune response is elicited against a second epitope on the antigen.

20 Claims, 4 Drawing Sheets

U.S. PATENT DOCUMENTS

| | | | |
|---|---|---|---|
| 6,358,976 | B1 | 3/2002 | Wityak et al. |
| 6,881,405 | B2 | 4/2005 | Leveugle et al. |
| 7,198,928 | B2 | 4/2007 | Liang et al. |
| 7,238,786 | B2 * | 7/2007 | Gold et al. ............. 530/387.3 |
| 2001/0036457 | A1 | 11/2001 | Madiyalakan et al. |
| 2002/0022235 | A1 | 2/2002 | Noujaim |
| 2002/0173629 | A1 * | 11/2002 | Jakobovits et al. ...... 530/388.22 |
| 2005/0048059 | A1 | 3/2005 | Madiyalakan et al. |
| 2005/0063976 | A1 | 3/2005 | Schultes et al. |
| 2005/0260208 | A1 | 11/2005 | Eng et al. |
| 2006/0159688 | A1 | 7/2006 | Madiyalakan et al. |
| 2007/0036798 | A1 | 2/2007 | Madiyalakan et al. |
| 2007/0092522 | A1 | 4/2007 | Noujaim |
| 2008/0131443 | A1 | 6/2008 | Madiyalakan et al. |
| 2008/0206318 | A1 | 8/2008 | Madiyalakan |
| 2008/0220012 | A1 | 9/2008 | Madiyalakan |
| 2008/0311127 | A1 | 12/2008 | Schultes et al. |
| 2009/0112163 | A1 | 4/2009 | Bivin et al. |
| 2009/0202560 | A1 | 8/2009 | Madiyalakan et al. |
| 2009/0291075 | A1 | 11/2009 | Eng et al. |

FOREIGN PATENT DOCUMENTS

| | | | |
|---|---|---|---|
| WO | WO 89/05140 | | 6/1989 |
| WO | WO 90/03142 | | 4/1990 |
| WO | PCT/US90/03142 | | 6/1990 |
| WO | WO 90/15626 | | 12/1990 |
| WO | WO 92/11334 | | 7/1992 |
| WO | PCT/US92/11334 | | 7/1993 |
| WO | WO 93/12819 | | 7/1993 |
| WO | WO 93/20185 | | 10/1993 |
| WO | WO 94/01719 | | 1/1994 |
| WO | PCT/EP94/01719 | | 8/1994 |
| WO | WO 94/21287 | | 9/1994 |
| WO | WO 94/27637 | | 12/1994 |
| WO | WO 95/04548 | | 2/1995 |
| WO | WO096/10400 | * | 4/1996 |
| WO | WO 97/42973 | | 11/1997 |
| WO | WO 98/57661 | | 12/1998 |
| WO | WO 99/65517 | | 12/1999 |
| WO | WO 01/00245 | | 1/2001 |
| WO | WO 01/07082 | | 2/2001 |
| WO | WO 01/12217 | | 2/2001 |
| WO | WO 01/59452 | | 8/2001 |
| WO | WO 01/85204 | | 11/2001 |
| WO | WO 02/076384 | | 10/2002 |
| WO | WO 03/034977 | | 5/2003 |
| WO | WO02004/032962 | * | 4/2004 |

OTHER PUBLICATIONS

Henry et at (Clinical Pharmacokinetics, 1992, vol. 23, pp. 85-89).*
Slapak and Kufe, 'Principles of Cancer Therapy', In: Harrison's Principles of Internal Medicine, 1994, Isselbacher et al, Ed.s, p. 1835.*
Abstract of Bukowski et al (Journal of Immunotherapy with Emphasis on Tumor Immunology, May 1994, vol. 15, pp. 273-282).*
Abstract of Stillwagon et al (International Journal of Radiation Oncology, Biology and Physics, 1991, vol. 20, pp. 65-71).*
Masucci et al (Medical Oncology and Tumor Pharmacotherapy, 1991, vol. 8, pp. 207-220).*
Frodin et al (Hybridoma, 1991, vol. 10, pp. 421-431).*
Chachoua et al (Journal of Immunotherapy, 1994, vol. 16, pp. 132-141).*
Segerling et al (Science, 1975, vol. 188, pp. 55-57.*
Abe et al (Journal of Immunological Methods, 2002, vol. 270, pp. 227-233).*
Balzer et al (Journal of Molecular Medicine, 1999, vol. 77, pp. 699-712).*
Imoto et al (Int J Cancer, 2006, vol. 120, pp. 357-361).*
Baars et al (British Journal of Cancer, 2002, vol. 86, pp. 1230-1234).*
Abbas, et al., "Antigen presentation by B lymphocytes," in Antigen Presenting Cells: Diversity, Differentiation, and Regulation, 1988, pp. 269-279.
Adams, et al., "Comparison of metabolic and receptor imaging in recurrent medullary thyroid carcinoma with histopatholooical findings," Eur J Nucl Med., 1988, vol. 25, No. 9, pp. 1277-1283.

"AltaRex Corp, (AXO) Reports Favorable OvaRex®, Phase II Trial Results", Biospace, AltaRex Corp., Jan. 13, 2001, p. 1.
Alzona, et al., "IL-12 activates IFN-gamma production through the preferential activation of CD30+ T cells," J Immunol., 1995, vol. 154, No. 1,1 pp. 9-16.
An, et al., "Biochemical and Functional Antigenic Mimicry by a Polyclonal Anti-Idiotypic Antibody for Chlamydial Exoglycolipid Antigen," Pathobiology, 1997, vol. 65, pp. 229-240.
Andersson, et al., "Modulation of antigen-antibody complexations by immunoglobulins," Scand J Immunol., 1995, vol. 42, No. 4, pp. 407-417.
Avigan, "Dendritic development, and potential immunotherapy", Blood Reviews, 1999, vol. 11, pp. 51-64.
Barnd, et al., "Specific, major histocompatibility complex-unrestricted recognition of tumor-associated mucins by human cytotoxic T cells," Proc Natl Acad Sci USA., 1989, vol. 86, No. 18, pp. 7159-7163.
Bartoloni, et al., "Assay, isolation and characterization of circulating immune complexes from serum of gastrointestinal cancer, stage III and IV melanoma and chronic inflammatory bowel disease patients," Oncology, 1993, vol. 50, No. 1, pp. 27-34.
Baskin, et al, "Moloney Leukemia Virus-Induced Cell Surface Antigen Mimicry by Monoclonal Antibodies", Immunol Res, 1995, vol. 14, pp. 292-316.
Bast, Jr., et al., "A radioimmunoassay using a monoclonal antibody to monitor the course of epithelial ovarian cancer," New England J. Med., 1983, vol. 309, No. 15, pp. 883-887.
Berek, "Immunotherapy of ovarian cancer with antibodies: a focus on oregovomab," Expert Opin. Biol. Ther., vol. 4(7), 2004, pp. 1159-1165.
Berlyn, et al., "Generation of CD4+ and CD8+ T Lymphocyte Responses by Dendritic Cells Armed with PSA/Anti-PSA (Antigen/Antibody) Complexes," Clinical Immmunology, Dec. 2001, vol. 101, No. 3, pp. 276-283.
Bernard, et al., " Possible Role for Specific Surface Immunoglobulin in Antigen Presentation," Antigen Presenting Cells: Diversity, Differentiation, and Regulation, 1988, pp. 291-300.
Betakova, et al., "Monoclonal Anti-Idiotypic and Antibodies Mimicking the Immunodominant Epitope of Influenza Virus Haemagglutinin Elicit Biologically Significant Immune Responses," Journal of General, Virology, 1998, vol. 79, pp. 461-470.
Bhattacharya-Chatterje et al., "Idiotypic antibody immunotherapy of cancer," Cancer Immunology, Immunotherapy, 1994, vol. 38, No. 2, pp. 75-82.
Bjork, "Short Analytical Review: Development of Dendritic Cells and Their use in Tumor Therapy", Clinical Immunology, 1999, vol. 92, pp. 119-127.
Boon, et al., "Tumor antigens recognized by T lymphocytes," Annu Rev Immunol., 1994, vol. 12, pp. 337-365.
Bouige, et al., "Immune complexes as immunizing agents to increase the number of monoclonal antibody-producing hybrids and to deviate the response to poorly immunogenic epitopes," Hybridoma, 1990, vol. 9, No. 6, pp. 519-526.
Brakenhoff, et al., "Construction and characterization of the chimeric monoclonal antibody E48 for therapy of head and neck cancer," Cancer Immunol Immunother., 1995, vol. 40, No. 3, pp. 191-200.
Bretscher, et al., "Establishment of stable, cell-mediated immunity that makes "susceptible" mice resistant to Leishmania major," Science, 1992, vol. 257, No. 5069, pp. 539-542.
Brockmeyer, et al., "Immunomodulation of cimetidine in healthy volunteers," Klin Wochenschr., 1989, vol. 67, No. 1, pp. 26-30.
Brukner, et al., "OvaRex AltaRex, Idrugs", The Investigational Drugs Journal, Apr. 2001, vol. 4, No. 4, pp. 457-462.
Bukowski, et al., "Phase I trial of continuous infusion interleukin-2 and doxorubicin in patients with refractory malianancies," J Immunother., 1991, vol. 10, No. 6, pp. 432-439.
Canevari, et al., "Regression of advanced ovarian carcinoma by intraperitoneal treatment with autologous T lymphocytes retargeted by a bispecific monoclonal antibody," J Natl Cancer Inst., 1995, vol. 87, No. 19, pp. 1463-1469.
Clackson, "Genetically enginEred monoclonal antibodies", Br. J. Rheumatol., 1991, vol. 3052, pp. 36-39.

Cocchi, et al., "Comparison Between Direct Binding, Competition and Agglutination Assays in the Characterization of Polyclonal Anti-Idiotypes Against Anti-HBs Human Monoclonal Antibodies," Journal of Immunolocical Methods, 1993, vol. 160, pp. 1-9.

Coccia, et al., "High Titer, Prostate Specific Antigen-Specific Human IgG Production by hu-PBL-SCID Mice Immunized with Antigen-Mouse IgG2a Complex-Pulsed Autologous Dendritic Cells", Journal of Immunology, Nov. 15, 1998, vol. 161, No. 10, pp. 5772-5780.

Cole, et al., Monoclonal Antibodies and Cancer Therapy, 1985, pp. 77-96, Alan R. Liss, Inc.

Coughlan, et al., "Enhanced proliferation of CD4+ T cells induced by dendritic cells following antigen uptake in the presence of a specific antibody", Veterinary Immunology and Immunopathology, 1996, vol. 49, pp. 321-330.

Crum, "Effect of cisplatin upon expression of in vivo immune tumor resistance," Cancer Immunol Immunother., 1993, vol. 36, No. 1, pp. 18-24.

Defoin et al., "A new liquid phase actinometer: quantum yield and photo-CIDNP study of phenylglyoxylic acid in aqueous solution," Journal of Photochemistry, 1986, Vol. 33, pp. 237-255.

Denardo, et al., "Synergy of Taxol and radioimmunotherapy with yttrium-90-Labeled chimeric L6 antibody: efficacy and toxicity in breast cancer xenografts", Proceedings of the National Academy of Sciences of the United States of America, Apr. 15, 1997, Vol. 94, No. 8, pp. 4000-4004.

Dhodapkar, et al, "Antitumor monoclonal antibodies enhance cross-presentation of Cellular antigens and the generation of myeloma-specific killer T cells by dendritic cells", The Journal of Experimental Medicine, Jan. 7, 2002, vol. 195, No. 1, pp. 125-133.

Dhodapkar, et al, "Rapid generation of broad T-cell immunity in humans after a single injection of mature dendritic cells", Journal of Clinical Investigation, 1999, vol. 104, No. 2, pp. 371-380.

Dileo, et al., "High resolution removal of virus from protein solutions using a membrane of unique structure," Biotechnology, 1992, vol. 10, No. 2, pp. 182-188.

Dileo, et al., "Size exclusion removal of model mammalian viruses using a unique membrane system, Part I: Membrane qualification," Biologicals, 1993, vol. 21, No. 3, pp. 275-286.

Dileo, et al., "Size exclusion removal of model mammalian viruses using a unique membrane system, Part II: Module qualification and process simulation," Biologicals, 1993, vol. 21, No. 3, pp. 287-296.

Dillman, "Monoclonal Antibodies for Treating Cancer", Annals of Internal Medicine, 1989, vol. 111, pp. 592-603.

Dillman, et al., "Continuous Infusion of Y101 Monocolonal Antibody in Chronic Lymphocytic Leukemia and Cutanious T-Cell Lymphoma", Journal of Biological Response Modifiers, 1986, vol. 5, pp. 394-410.

Dixon, "Evaluation of the CASPO2 Docking Section", Proteins, 1997, Proteins: Structure, Function, and Genetics, Suppl. 1, pp. 198-204.

Dohlsten, et al., "Antibody-targeted superantigens are potent inducers of tumor-infiltrating T lymphocytes in vivo," Proc Natl Acad Sci USA., 1995, vol. 92, No. 21, pp. 9791-9795.

Dohlsten, et al.,"Monoclonal antibody-superantigen fusion proteins: tumor-specific agents for T-cell-based tumor therapy," Proc Natl Acad Sci USA., 1994, vol. 91, No. 19, pp. 8945-8949.

Dong, et al., "Cytokines as Vaccine Adjuvants:Current Status and Potential Applications," Vaccine Design: The Subunit and Adjuvant Approach, Powell et al, Ed., 1995, Chapter 27, pp. 625-643.

Donnerstag, et al., "Immunological profile of patients with ovarian cancer under immunostimulation with murine monoclonal antibodies," International J. of Oncology, 1995, vol. 6, pp. 853-858.

Dorai, et al., "Aglycosylated chimeric mouse/human IgG1 antibody retains some effector function," Hybridoma, 1991, vol. 10, pp. 211-217.

Douillard, et al., "Immunohistochemical Antigenic Expression and in Vivo Tumor Uptake of Monoclonal Antibodies with Specificity for Tumors of the Gastrointestinal Tract", Cancer Research, Aug. 1986, vol. 46, pp. 4221-4224.

Durrant, et al., "Enhanced cell-mediated tumor killing in patients immunized with human monoclonal antiidiotypic antibody 105A07," Cancer Res., 1994, vol. 54, No. 18, pp. 4837-4840.

Ehlen, et al., "Induction of tumor protective Immunity utilizing the CA125 specific monoclonal, OvaRex, Mab-B43.13, In a cohort of patients with advanced recurrent ovarian cancer", Thirty-second Annual Meeting of the Society of Gynecologic Oncologists, Nashville, Tennesse, Mar. 3-7, 2001 (Abstract only).

Ehrke, et al., "Effects of anticancer drugs on the immune system in humans," Semin Oncol., 1989, vol. 16, No. 3, pp. 230-253.

Fagerberg, et al., "Induction of an immune network cascade in cancer patients treated with monoclonal antibodies (ab1). I. May induction of ab1-reactive T cells and anti-anti-idiotypic antibodies (ab3) lead to tumor regression after mAb therapy?", Cancer Immunol Immunother., 1993, vol. 37, No. 4, pp. 264-270.

Fagerberg, et al., "Induction of an immune network cascade in cancer patients treated with onoclonal antibodies (ab1). II. Is induction of anti-idiotype reactive T cells (T3) of importance for tumor response to mAb therapy? ", Cancer Immunol Immunother., 1994, vol. 38, No. 3, pp. 149-159.

Fagerberg, et al., "Tumor regression in monoclonal antibody-treated patients correlates with the presence of anti-idiotype-reactive T lymohocytes", Cancer Res, 1995, vol. 55, No. 9, pp. 1824-1827.

Fendrick, et al., "Characterization of CA 125 synthesized by the human epithelial amnion WISH cell line, " Tumour Biol., 1993, vol. 14, No. 5), pp. 310-318.

Foon, et al., "Clinical and Immune Responses in Advanced Colorectal Cancer Patients Treated with Anti-Idiotype Monoclonal Antibody Vaccine that Mimics the Carcinoembryonic Antigen," Clinical Cancer Research, 1997, vol. 3, pp. 1267-1276.

Gadducci, et al., "Serum half-life of CA 125 during early chemotherapy as an independent prognostic variable for patients with advanced epithelial ovarian cancer: results of a multicentric Italian study," Gynecol Oncol., 1995, vol. 58, No. 1, pp. 42-47.

Gallagher, et al., "Adoptive immunotherapy of experimental ovarian cancer using activated human monocytes and the human monoclonal antibody, anti-14C1 ," Intl J of Ohcology, 1994, vol. 5, pp. 253-258.

Gallagher, et al., "Multiple epitopes of the human ovarian cancer antigen 14C1 recognised by human IaG antibodies: their potential in immunotherapy," Br J Cancer, 1991, vol. 64, No. 1, pp. 35-40.

Geffner, et al., " Activation of human neutrophils and monocytes induced by immune complexes prepared with cationized antibodies or antigens," Clin Immunol Immunopathol., 1993, vol. 69, No. 1, pp. 9-15.

Goldenberg, "New developments in monoclonal antibodies for cancer detection and therapy," CA CancerJ Clin., 1994, vol. 44, No. 1, pp. 43-64.

Goronzy, et al., "Long-term humoral unresponsiveness in vivo, induced by treatment with monoclonal antibody against L3T4," J EXf Med., 1986, vol. 164, No. 3, pp. 911-925.

Greenspan, et al. "Idiotypes: structure and immunogenicity" The FASEB Journal, 1993, vol. 7, pp. 437-444.

Hamanaka, et al., "Sialyl Lewisa Ganglioside in Pancreatic Cancer Tissue Correlates with the Serum CA 19-9 Level," Pancreas, 1996, vol. 13, pp. 160-165.

Handgretinger, et al., "A phase I study of human/mouse chimeric anti-ganglioside GD2 antibody ch14.18 in patients with neuroblastoma," Eur J Cancer, 1995, vol. 31A, No. 2), pp. 261-267.

Hariharan, et al., "The induction of cytotoxic T cells and tumor regression by soluble antigen formulation," Cancer Res., 1995, vol. 55, No. 16, pp. 3486-3489.

Hertel, et al., "A New Tc-99m Labeled Monoclonal Antibody (B43.13) Against CA 125 for Early Detection of Ovarian Cancer Recurrences-First Clinical Results," Proceedings of the 39th Annual Meeting, 1992, vol. 33, No. 5, p. 904, abstract 338.

Hoskins, et al., "Ten-year outcome of patients with advanced epithelial ovarian carcinoma treated with cisplatin-based multimodality therapy," J Clin Oncol., 1992, vol. 10, No. 10, pp. 1561-1568.

Hozumi, et al., "Recombinant antibody technology: its advent and advances," Cancer Invest., 1993, vol. 11, No. 6, pp. 714-723.

Ioannides, et al., "Cytotoxic T cells from ovarian malignant tumors can recognize polymorphic epithelial mucin core peptides," J Immunol., 1993, vol. 151, No. 7, pp. 3693-3703.

Iribe, et al., "Characterization of the Antibody Response Against the Type II Collagen Induced by Anti-Idiotypic Antibody," Cellular Immunology, 1990, vol. 128, pp. 400-411.

Jacoby, et al., "Characterization of mouse parvovirus infection by in situ hybridization," J Virol., 1995, vol. 69, No. 6, pp. 3915-3919.

Jain, "Barriers to Drug Delivery in Solid Tumors", Scientific America, Jul. 1994, vol. 271, No. 1, pp. 58-65.

Jensen, et al., "Possible utility of serum determinations of CA 125 and CA 27.29 in breast cancer management," Int. J. Biol. Markers, 1991, vol. 6, No. 1, pp. 1-6.

Jerne, "Towards a network theory of the immune system," Ann Immunol (Paris), 1974, vol. 125C(1-2), pp. 373-389.

Jiang, et al., "a Novel Peptide Isolated froma Phage Display Peptide Library with Trastuzumab Can Mimic Antigen Epitope of HER-2", The Journal of Biological Chemistry, Feb. 11, 2005, vol. 280, No. 6, pp. 4656-4662.

Joliffe, "Humanized Antibodies: Enhancing Therapeutic Utility Through Antibody Engineering" Internal Rev. Immun., 1993, vol. 10, pp. 241-250.

Jones, et al., "Replacing the complementarity-determining regions in a human antibody with those from a mouse", Nature, May 29, 1986, vol. 321, pp. 522-525.

Khazaeli, et al., "Human immune response to monoclonal antibodies," J. Immunother., 1994, vol. 15, No. 1, pp. 42-52.

Kim, et al., "Gamma delta T cell recognition of tumor Ig peptide," J Immunol., 1995, vol. 154, No. 4, pp. 1614-1623.

Kim, et al., "The role of apoptosis in cancer cell survival and therapeutic outcome", Cancer Biology & Therapy, 2006, vol. 5, No. 11, pp. 1429-1442.

Klug, et al., "Tumororigency in Athymic Mice of the Human Colon Carcinoma Cell Line SW1116 Expressing the Tumor-associated Antigenic Determinant CA 19-9", Cancer Research, 1984, vol. 44, pp. 1048-1053.

Knuth, et al., "T-cell-mediated cytotoxicity against autologous malignant melanoma: analysis with interleukin 2-dependent T-cell cultures," Proc Natl Acad Sci. U.S.A., 1984, vol. 81, No. 11, pp. 3511-3515.

Kobayashi, et al., "Characterization of CA 125 antigen identified by monoclonal antibodies that recognize different epitopes", Clin Biochem., 1993, vol. 26, pp. 391-397.

Kohler et al., "Continuous cultures of fused cells secreting antibody of predefined specificity", Nature, 1975, vol. 256, pp. 495-497.

Kohler, S. et al., "Immuntherapie des Ovarial-karzinoms mit dem monoklonalen anti-idiotypischen Antikorper ACA125-Ergebnisse der Phase-ib-Studie," Gynakologische Tumoren, 1998, vol. 58, pp. 180-186 (English translation included).

Kosmas, et al., "Activation of cellular immunity after intracavitary monoclonal antibody therapy of ovarian cancer," Cancer, 1994, vol. 73, No. 12, pp. 3000-3010.

Kosmas, et al., "Patients receiving murine monoclonal antibody therapy for malignancy develop T cells that proliferate in vitro in response to these antibodies as antigens," Br J Cancer, 1991, vol. 64, No. 3, pp. 494-500.

Kozbor, et al., "The production of monoclonal antibodies from human lymphocytes" Immunology Today, 1983, vol. 4, pp. 72-79.

Kreutz, et al., "Biospecific monoclonal Anti-CA 125 X Anti-peroxidase antibodies in the measurement of the ovarian carcinoma antigen" J of Tumor Marker Oncology, 1995, vol. 10, No. 1, pp. 45-53.

Lamers, et al., "Inhibition of bispecific monoclonal antibody (bsAb)-targeted cytolysis by human anti-mouse antibodies in ovarian carcinoma patients treated with bsAb-targeted activated T-lymphocytes," Int J Cancer, 1995, vol. 60, No. 4, pp. 450-457.

Lanzavecchia, et al., "Antibodies as antigens. The use of mouse monoclonal antibodies to focus human T cells against selected targets", J Exp Med., 1988, vol. 167, No. 2, pp. 345-352.

Lensink, et al., "Docking and scoring protein complexes: CAPRI 3rd Edition", Proteins, 2007, Vol. 69, pp. 704-718.

Leveugle, et al., "PSA-directed immunotherapy of prostate cancer", Proceedings of the American Associate for Cancer Research Annual Meeting, Mar. 1998, vol. 39, p. 355.

Ling, et al., "Modulation of the murine immune response to human IgG by complexing with monoclonal antibodies," Immunology, 1987, vol. 62, pp. 7-10.

Livingston, et al., "Symposium 10: glucosylation defining malignancy. Effect of active immunization with human tumor associated carbohydrate antigens on the immune response and on tumor Qrowth," Proc. Am. Assoc. Cancer Research, 1995, vol. 36, p. 678.

Lobuglio, et al., "Phase I Trial of Multiple Large Doses of Murine Monoclonal Antibody CO17-1A. I. Clinical Aspects", Journal of the National Cancer Institute, Aug. 17, 1988, vol. 80, No. 12, pp. 932-936.

Lopes, et at., "Liposome-mediated delivery stimulates a class I-restricted cytotoxic T cell response to soluble antigen," Eur J Immunol., 1992, vol. 22, No. 1, pp. 287-290.

Ma, et al., "Induction of anti-idiotypic humoral and cellular immune responses by a murine monoclonal antibody recognizing the ovarian carcinoma antigen CA125 encapsulated in biodegradable microspheres", Cancer immunol. immunother., 1998, vol. 47 pp. 13-20.

Manca, et al., "Differential Activation of T Cell Clones Stimulated by Macrophages Exposed to Antigen Complexed with Monoclonal Antibodies," J Immunol., 1988, vol. 140, pp. 2893-2898.

Manca, et al., "Effect of antigen/antibody ratio on macrophage uptake, processing, and presentation to T cells of antigen complexed with polyclonal antibodies," J Exp Med., 1991, vol. 173, No. 1, pp. 37-48.

Maraveyas, "Targeted immunotherapy. An update with special emphasis on ovarian cancer", Acta Oncol., 1993, vol. 32, Nos. 7-8, pp. 741-746.

Martin, et al., "Modeling antibody hypervariable loops: a combined algorithm," Proc Natl Acad Sci USA, 1989, vol. 86, pp. 9268-9272.

Marusic-Galesic, et al., "Cellular immune response to the antigen administered as an immune complex", Immunology, 1991, vol. 72, No. 4, pp. 526-531.

Marx, "Antibodies made to order", Science, 1985, vol. 229, pp. 455-456.

Meier, "CA 125 based diagnosis and therapy in recurrent ovarian cancer," Abstracts of the Eighth International Hamburg Symposium on Tumor Markers Hamburg, Dec. 1995, Germany, p. 2443, Abstract 179.

Moingeon, "Cancer Vaccines", Vaccine, 2001, vol. 19, pp. 1305-1326.

Mosmann, et al., "Two types of mouse helper t-cell clone, (review)", Immunology Today, 1987, Vol. 8 Nos. 7-8, pp. 223-227.

Muddukrishna, et al., "Indirect iodometric procedure for quantation of Sn(II) in radiopharmaceutical kits," Appl. Radial. Isot., 1994, vol. 45, No. 3, pp. 293-299.

Munn, et al., "Interleukin-2 enhancement of monoclonal antibody-mediated cellular cytotoxicity against human melanoma," Cancer Res., 1987, vol. 47, No. 24 Pt. 1, pp. 6600-6605.

Nap, et al, "Immunohistochemical characterization of 22 monoclonal antibodies against the CA125 antigen": 2nd report from the ISOBM TD-1 workshop, Tumor Biology, 1996, vol. 17, pp. 325-331.

Naramura, et al., "Therapeutic potential of chimeric and murine anti-(epidermal growth factor receptor) antibodies in a metastasis model for human melanoma," Cancer Immunol Immunother., 1993, vol. 37, No. 5, pp. 343-349.

Nicodemus, et al., "Immunomodulation with antibodies: clinical application in ovarian cancer and other malignancies," Expert Rev. Vaccines, 2002, vol. 1, No. 1, pp. 35-48.

Nonoyama, et al.," Strain-Dependent Leakiness of Mice with Severe Combined Immune Deficiency", J. Imm., 1993, vol. 150, pp. 3817-3824.

Noujaim, "Induction of CA125—Specific B and T Cell Responses in Patients Injected with Mab-B43.13—Evidence for Antibody-Mediated Antigen-Processing and Presentation of CA125 in Vivo,"Cancer Biotherapy & Radiopharmaceuticals, 2001, vol. 16, No. 3, pp. 187-203.

Nouwen, et al., "Tumor Markers in the Human Ovary and Its Neoplasms: A Comparative Immunohistochemical Study", Am. J. Path., 1987, vol. 126, pp. 230-242.

Nustad, et al. "Specificity and affinity of 26 monoclonal antibodies against the CA 125 antigen:" First report from the ISOBM TD-1 workshop, Tumor Biology, 1996, vol. 17, pp. 196-219.

Ohta, et al., "Tumor-associated glycoantigen, sialyl Lewis.sup.a as a target for bispecific antibody-directed adoptive tumor immunotherapy," Immunol Lett., 1995, vol. 44, No. 1, pp. 35-40.

Oltrogge, et al., "Generation of human monoclonal anti-idiotypic antibodies with specificity to the murine monoclonal anti-CA 125 antibody B43.13", The International Journal of Biological Markers, Oct.-Dec. 1996, vol. 11, No. 4, pp. 211-215.

"Ovarian Cancer: Screening, Treatment, and Followup", NIH Consens Statement, 1994, vol. 12, No. 3, 39 pages.

Ozols, "Biologic Treatment of Human Cancer," Current Problems in Cancer, 1995, vol. 19, No. 4, pp. 190-261.

Paul, Fundamental Immunology, 3rd Edition, 1993, p. 423, Raven Press, New York.

Perala-Heape, et al., "Effects of tumour mass and circulating antigen on the biodistribution of 111 in-labelled F(ab')2 fragments of human prostatic acid phosphatase monclonal antibody in nude mice bearing PC-82 human prostatic tumour xenografts," Eur J Nucl Med., 1991, vol. 18, No. 5, pp. 339-345.

Percy, et al., "Monoclonal Anti-Idiotypic and Anti-Anti-Idiotypic Antibodies from Mice Immunized with a Protective Monclonal Antibody Against Schistosoma Mansoni," The Journal of Immunology, 1988, vol. 140, pp. 82760-82762.

Pierce, "Receptor-Mediated B-Cell Antigen Processing: Increased Antigenicity of a globular protein covalently coupled to antibodies specific for B cell surface structures" The Journal of Immunology, 1988, vol. 140, No. 2, pp. 404-410.

Pimm, et al., "Influence of syngeneic monoclonal anti-idiotypic antibodies to murine monoclonal antibodies against tumour-associated antigens on the biodistribution of their target antibodies and their fraqrnents," J Cancer Res Clin Oncol., 1993, vol. 119, No. 7, pp. 408-414.

Pimm, et al., "Toxicity associated with the formation and clearance of immune complexes between antitumour monoclonal antibodies and syngeneic anti-idiotypic antibodies in mice," J Cancer Res Clin Oncol., 1992, vol. 119, No. 1, pp. 41-45.

Pimm, et al., "Circulating antigen: bad or good for immunoscintigraphy?" Nucl Med Biol., 1995, vol. 22, No. 2, pp. 137-145 (review).

Provencher, et al., "Estimation of globular protein secondary structure from circular dichroism," Biochemistry, 1981, vol. 20, No. 1, pp. 33-37.

Qi, et al., "Characterization of an anti-MUC1 monoclonal antibody with potential as a cancer vaccine," Hybridoma and Hybridomics, 2001, vol. 20, pp. 313-324.

Qi, et al., "Induction of idiotype network to anti-MUC-1 antibody in breast cancer," Proceedings of the American Association for Cancer Research Annual, 1998, vol. 39, p. 367.

Randall, et al., "Purification of antibody-antigen complexes containing recombinant SIV proteins: comparison of antigen and antibody-antigen complexes for immune priming," Vaccine, 1994, vol. 12, No. 4, pp. 351-358.

Ravindranath, et al, "Endothelial-Selectin Ligands Sialyl Lewisx and Sialyl Lewisa Are Differentiation Antigens Immunogenic in Human Melanoma", Cancer, 1997, vol. 79, p. 1686-1697.

Riechmann, et al., "Reshaping human antibodies for therapy", Nature, Mar. 24, 1988, vol. 332, No. 6162, pp. 323-327.

Reinhartz, et al., "Evaluation of Immunological Responses in Patients with Ovarian Cancer Treated with the Anti-idiotype Vaccine ACA 125 by Determination of Intracellular Cytokines—A Preliminary Report", HYBRIDOMA, 1999, vol. 18, pp. 41-45.

Regnault, et al., "Fcg Receptor-mediated Induction of Dendritic Cell Maturation and Major Histocompatibility Complex Class I-restricted Antigen Presentation after Immune Complex Internalization", J. Exp. Med., 1999, vol. 189, pp. 371-380.

Riethmüller, et al., "Randomised trial of monoclonal antibody for adjuvant therapy of resected Dukes' C colorectal carcinoma," Lancet, 1994, vol. 343, No. 8907, pp. 1177-1183.

Riethmüller, et al., "Monoclonal antibodies in cancer therapy," Curr Opin Immunol., 1993, vol. 5, No. 5, pp. 732-739.

Rodkey, "Studies of Idiotypic Antibodies: Production and Characterization of Autoantiidiotypic Antisera" Exp. Med., 1974, vol. 130, pp. 712-720.

Rodwell, "EnginEring monoclonal antibodies", Nature, Nov. 2, 1989, vol. 342, pp. 99-100.

Ron, et al., "Use of CA-125 response to predict survival parameters of patients with advanced ovarian carcinoma", Acta Obstet Gynecol Scand., 1994, vol. 73, No. 8, pp. 658-662.

Roosnek, et al., "Efficient and selective presentation of antigen-antibody complexes by rheumatoid factor B cells", J Exp Med, 1991, vol. 173, No. 2, pp. 487-489.

Russo, et al., "Apoptosis: a relevant tool for anticancer therapy", Annals of oncology : official journal of the European Society for Medical Oncology / ESMO, Jun. 2006, vol. 17, pp. 115-123.

Saga, et al, "An antibody-tumor model for the targeting of CA125-producing gynecologic malignancies", Jpn. J. Can. Res., 1990, vol. 81, pp. 1141-1148.

Scher, "HER2 in prostate cancer—a viable target or innocent bystander?", Journal of the National Cancer Institute, Dec. 6, 2000, vol. 92, No. 23, pp. 1866-1868.

Schlebusch, et al., "A monoclonal antiidiotypic antibody ACA 125 mimicking the tumor-associated antigen CA 125 for immunotherapy of ovarian cancer," Hybridoma, 1995, vol. 14, No. 2, pp. 167-7.

Schoenfeld, "Idiotypic induction of autoimmunity: a new aspect of the idiotypic network," The FASEB Journal, 1994, vol. 8, pp. 1296-1301.

Schmolling, et al., "Antiidiotypic antibodies in ovarian cancer patients treated with the monoclonal antibody B72.3," Hybridoma, 1995, vol. 14, No. 2, pp. 183-186.

Schultes, et al., "Idiotypic cascades after injection of the monoclonal antibody OC125: a study in a mouse model. Induction of antibodies against OC125 and CA125 after immunization with an anti-CA125 (MAb OC125) monoclonal antibody by activation of the idiotypic network," Eur J Clin Chem Clin Biochem, 1993, vol. 31, No. 7, pp. 427-432.

Schultes, et al., "Anti-idiotype induction therapy: anti-CA 125 antibodies (Ab.sub.3) mediated tumor killing in patients treated with Ovarex mAb B43.13 (Ab.sub.1)", Cancer Immunol Immunother, Jun. 1998, vol. 46, No. 4, pp. 201-212.

Schultes, et al., "Antibody-antigen immune complexes allow for efficient MHC class I and II-restricted antigen presentation and maturation of dendritic cells: a novel strategy for cancer immunotherapy", Proceedings of the 92nd Annual Meeting of The American Association for Cancer Research, New Orleans, LA, Mar. 24-28, 2001, Proeedings of the Annual Meeting of the American Association for Cancer Research, Philadelphia, PA: ACCR, US, Mar. 24, 2001, vol. 42, p. 276 (Abstract only).

Schultes, et al., Induction of tumor- and CA 125-specific T cell responses in patients (pts) with epithelial ovarian cancer (EOC) treated with OveRex®, ProcEdings of the American Association for Cancer Research, Mar. 2002, vol. 43, p. 144 (Abstract only).

Schultze et al., "DCs and CD40-activated B cells: current and future avenues to Cellular Cancer Immunotherapy," Trends in Immunology, 2004, vol. 25, pp. 659-664.

Sciammas, et al., "TCR gamma delta cells: mysterious cells of the immune system," Immunol Res., 1994, vol. 13, No. 4, pp. 268-279.

Sears, et al., "Effects of Monoclonal Antibody Immunotherapy on Patients with Gastrointestinal Adenocarcinoma", Journal of Biological Response Modifiers, 1984, vol. 3, pp. 138-150.

Sears, et al., "Phase II Clinical Triual of a Murine Monoclonal Antibody Cytotoxic for Gastrointestinal Adenocarcinoma", Cancer Research, Nov. 1985, vol. 45, pp. 5910-5913.

Seferian, et al., "Antibody Synthesis Induced by Endogenous Internal Images," Applied Biochemistry and Biotechnology, 1994, vol. 47, pp. 213-227.

Shitara, et al., "A mouse/human chimeric anti-(ganglioside GD3) antibody with enhanced antitumor activities," Cancer Immunol Immunother., 1993, vol. 36, No. 6, pp. 373-380.

Shulof, "Phase II Trial of Thymosin Fraction 5 in Advanced Renal Cancer", Journal of Biological Response Modifiers, 1984, vol. 3, No. 2, pp. 151-152.

Slamon, et al., "Use of chemotherapy plus a monoclonal antibody against HER2 for metastatic breast cancer that overexpresses HER2", The New England Journal of Medicine, Mar. 15, 2001, vol. 344, No. 11, pp. 783-792.

Squire, et al., "Antigen presentation is enhanced by targeting antigen to the Fc epsilon RII by antigen-anti-Fc epsilon RII conjugates," J Immunol., 1994, vol. 152, No. 9, pp. 4388-4396.

Stancovski, et al., "Mechanistic aspects of the opposing effects of monoclonal antibodies to the ERBB2 receptor on tumor growth", ProcEdings of the National Academy of Sciences USA, Oct. 1991, vol. 88, pp. 8691-8695.

Steinman, "The Dendritic Cell System and its Role in Immunogenicity", Annu. Rev. Immunol., 1991, vol. 2, pp. 271-296.

Striete, et al., "Cellular and molecular regulation of tumor necrosis factor-alpha production by pentoxifylline," Biochem Biophys Res Commun., 1988, vol. 155, No. 3, pp. 1230-1236.

Sulica, et al., "Regulation of human natural cytotoxicity by IgG. IV. Association between binding of monomeric IgG to the Fc receptors on large granular lymphocytes and inhibition of natural killer (NK) cell activity," CeliImmunol., 1993, vol. 147, No. 2, pp. 397-410.

Taggart, "Stable antibody-producing murine hybridomas," Science, 1983, vol. 219, pp. 1228-1230.

Tame, "Scoring functions: A view from the bench", Journal of Computer-Aided Molecular Design, 1999, vol. 13, pp. 99-108.

Tew, et al., "Induction of the secondary antibody response: immune complex formation, iccosome release by follicular dendritic cells, processing and presentation of antigen by genminal center b cells and tingible body macrophages," Progress in Leukocyte Biology, 1988, vol. 7, pp. 1-10, Alan R Liss, Inc., New York.

Timmerman, et al., "Dendritic Cell Vaccines for Cancer Immunotherapy", Annu. Rev. Med., 1999, vol. 50, pp. 507-529.

Torbett et al., "hu-PBL-SCID mice: a model for human immune function, AIDS, and lymphomagenesis," Immunological Reviews, 1991, vol. 124, pp. 139-164.

Trauth, et al., "Monoclonal antibody-mediated tumor regression by induction of apoptosis," Science, 1989, vol. 245, No. 4915, pp. 301-305.

Petrakou, et al., "Epitope mapping of anti-MUC1 mucin protein core monoclonal antibodies", Tumour biology : the journal of the International Society for Oncodevelopmental Biology and Medicine, 1998, vol. 19, Suppl. 1, pp. 21-29.

Rye, et al., "Summary report on the ISOBM TD-6 workshop: analysis of 20 monoclonal antibodies against Sialyl Lewisa and related antigens. Montreux, Switzerland, Sep. 19-24, 1997", Tumour biology : the journal of the International Society for Oncodevelopmental Biology and Medicine, 1998, vol. 19, No. 5, pp. 390-420.

Uemura, et al., "Generation of anti-idiotype antibodies related to prostatic specific antigen," Jpn J. Cancer Res., 1995, vol. 7, No. 10, p. 19 (meeting abstract).

Ullman, et al., "Anti-immune complex antibodies enhance affinity and specificity of primary antibodies," Proc Natl Acad Sci USA, 1993, vol. 90, No. 4, pp. 1184-1189.

Van Der Bruggen, "The Long-Standing Quest for Tumor Rejection Antigens," Clinical Immunology and Immunopathology, 1994, vol. 71, No. 3, pp. 248-252.

Verhoeyen, et al., "Reshaping human antibodies: grafting an antilysozyme activity", Science, Mar. 25, 1988, vol. 239, No. 4847, pp. 1534-1536.

Vivetta, "Monoclonal antibodies as agonists: an expanded role for their use in cancer therapy," Cancer Res., 1994, vol. 54, No. 20, pp. 5301-5309.

Vose, et al., "Specific cytotoxicity against autologous tumour and proliferative responses of human lymphocytes grown in interleukin 2", Int J Cancer, 1982, vol. 29, No. 1, pp. 33-39.

Wagner, "Antitumor antibodies for immunotherapy of ovarian carcinomas," Hybridoma, 1993, vol. 12, No. 5, pp. 521-528.

Wagner, et al., "Clinical courses of patients with ovarian carcinomas after induction of antiidiotypic anti bodies against a tumor-associated antigen," Tumor Diagnostik & Therapie, 1990, vol. 11, pp. 1-4.

Walker, et al., "Prolactin-immunoglobulin G complexes from human serum act as costirnulatory ligands causing proliferation of malignant B lymphocytes," Proc Natl Acad Sci USA, 1995, vol. 92, No. 8, pp. 3278-3282.

Wawrzynczak, et al., "Blood clearance in the rat of a recombinant mouse monoclonal antibody lacking the N-linked oligosaccharide side chains of the CH2 domains," Mol Immunol., 1992, vol. 29, pp. 213-220.

Weiner, "An Overview of Monoclonal Antibody Therapy of Cancer", Seminars in Oncology, Aug. 1999, vol. 26, 4 Suppl. 12, pp. 41-50.

White, et al. "Process Validation for Virus Removal and Inactivation" BioPharm, May 1991, pp. 34-39.

Wiersma, et al., "Enhancement of the antibody response to protein antigens by specific IgG under different experimental conditions," Scand J Immunol., 1992, vol. 36, No. 2, pp. 193-200.

Wolff, et al., "Monoclonal antibody homodimers: enhanced antitumor activity in nude mice," Cancer Res., 1993, vol. 53, No. 11, pp. 2560-2565.

Wyatt, "Light scattering and the absolute characterization of macromolecules" (review) Analytica Chimica Acta, 1993, vol. 272, pp. 1-40.

Xu, et al., "Overcoming suppression of antitumor immune reactivity in tumor-bearing rats by treatment with bleomycin," Cancer Res., 1988, vol. 48, No. 23, pp. 6658-6663.

Yano, et al., "Natural antibodies against the immunoglobulin F(ab')2 fragment cause elimination of antigens recognized by the F(ab')2 from the circulation," European Journal of Immunology, 1995, vol. 25, No. 11, pp. 3128-3133.

Yu, et al., "Genetic Control of Anti-Idiotypic Vaccination Against Coronavirus Infection," European Journal of Immunology, 1996, vol. 26, pp. 3230-3233.

Zhang, et al., "Increased tumor cell reactivity and complement-dependent cytotoxicity with mixtures of monoclonal antibodies against different gangliosides," Cancer Immunology Immunotherapy, 1995, vol. 40, No. 2, pp. 88-94.

Adkins at al., "Edrecolomab (Monoclonal Antibody 17-1A)", Drugs, 56(4): 619-626 (1998).

Algarra et al., "Altered MHC class I antigens in tumors", Int. J. of Clin. & Lab, 27:95-102 (1997).

Antonia et al., "Mechanisms of immune tolerance induction through the thymic expression of a peripheral tissue-specific protein", Int. Imm., 7:715-725 (1995).

Aquino et al., "Immune system recovery after treatment for Cancer", Infections in Medicine, 16(3):190-196 (1999).

Bachmann et al., "Regulation of IgG antibody titers by the amount persisting of immune-complexed antigen," Eur. J. Imm., 24:2567-70 (1994).

Baum et al., "Activating Anti-Idiotypic Human Anti-Mouse Antibodies for Immunotherapy of Ovarian Carcinoma". Cancer. 73:1121-25 (1994).

Benichou et al., "Disruption of the determinant hierarchy on a self-MHC peptide: concomitant tolerance induction to the dominant determinant and priming to the cryptic self-determinant", Int. Imm., 6:131-38 (1994).

Bodey et al., "Failure of Cancer Vaccines: The Significant Limitations of this Approach to Immunotherapy", Anticancer Res., 20:2665-2676 (2000).

Chattopadhyay et al., "Human high molecular weight-melanoma associated antigen mimicry by an anti-idiotypic antibody: characterization of the immunogenicity and the immune response to the mouse monoclonal antibody IMEl-1," Cancer Res., 5:6045-51 (1991).

Cibotti, PNAS, "Tolerance to a self-protein involves its immunodominant but does not involve its subdominant determinants", 89:416-20 (1992).

Clark, Protein Engineering of antibody Molecules for Prophylactic and therapeutic Applications in Man, (monograph), Prot. Eng., 1 (1993).

Crowley et al., "Dendritic cells are the principal cells in mouse spleen bearing immunogenic fragments of foreign proteins", J. Exp. Med., 172:383-386 (1990).

Davis et al., "Anti-idiotype antibodies can induce long-term complete remissions in non-Hodgkin's lymphoma without eradicating the malignant clone", Blood, 92(4):1184-1190 (1998).

De la Salle, "FcγR on Human Dendritic Cells", Human IgG Receptors, p. 39-55 (1996).

Fagerberg, "Humoral anti-idiotypic and anti-anti-idiotypic immune response in cancer patients treated with monoclonal antibody 17-1A," Cancer Imm., 12:81-87 (1996).
Frodin et al., Hybridoma, "Induction of anti-idiotypic (ab2) and anti-anti-idiotypic (ab3) antibodies in patients treated with the mouse monoclonal antibody 17-1A (ab1). Relation to the clinical outcome—an important antitumoral effector function?," 10:421-31 (1991).
Gold et al., "Characterization of monoclonal antibody PAM4 reactive with a pancreatic cancer mucin", Int. J. Cancer, 57:204-210 (1994).
Goldenberg et al., "Cancer Diagnosis and Therapy with Radiolabeled Antibodies", In: Immunoconjugates, Antibody Conjugates in Radioimaging and Therapy of Cancer, Vogel. Ed., 259-280 (1987).
Haller, "Update of Clinical Trials with Edrecolomab: a monoclonal antibody therapy for colorectal cancer", Seminars of Oncology, 28(1):25-30 (2001).
Harris et al., "The effect of immunosuppressive chemotherapy on immune function in patients with malignant disease", Cancer, 37:1058-1069.
Jumcic-Winkler, "Clinical evaluation of a new prostate-specific antigen sandwich ELISA which employs four monoclonal antibodies directed at different epitopes of prostate-specific antigen", Eur. Urol., 24:487-91 (1993).
Keder et al., "Cancer Immunotherapy: Are the results discouraging? Can they be improved?", Adv. Cancer Res., 59:245-323 (1992).
Klaus, "Antigen-antibody complexes elicit anti-idiotypic antibodies to self-idiotopes," Nature, 272:265-66 (1978).
Lee et al., "Increased Vaccine-Specific T Cell Frequency After Peptide-Based Vaccination Correlates with Increased Susceptibility to In Vitro Stimulation But Does Not Lead to Tumor Regression", J. Imm., 163:6292-300 (1999).
Leitzel, "Elevated Soluble c-erbB-2 Antigen Levels in the Serum and Effusions of a Proportion of Breast Cancer Patients", J. Clin. Oncol., 10:1436-1442 (1992).
McGuckin et al., "Circulating tumour-associated mucin concentrations, determined by the CASA assay, in healthy women," Clin. Chim. Acta, 214:139-51 (1993).
Ng et al., "Radiosensitization of tumor-targeted radioimmunotherapy with prolonged topotecan infusion in human breast cancer xenografts", Cancer Research, 61:2996-3001 (2001).
Nishimura, "The critical role of TH1-dominant immunity in tumor immunology, Cancer Chemother", Cancer/Chemo, 46:S52-S61 (2000).
Ohlen et al., "Expression of a Tolerizing Tumor Antigen in Peripheral Tissue Does Not Preclude Recovery of High-Affinity CB+ T Cells of CTL Immunotherapy of Tumors Expressing the Antigen", J. Imm., 166:2863-2870 (2001).
Pani et al., "Failure of presented, nondominant self epitope to induce tolerance—implications for autoimmune-diseases", Imm. Inv., 23:337-346 (1994).
Paul, "Factors limiting effective tumor immunity", Fund. Imm., 1163-69 (1993).
Rooijen, "The role of the FDC-retained immune complex network and its dynamics in the activity of germinal centres," Res. Immunol., 144:545-52 (1993).
Sallusto, "Efficient presentation of soluble antigen by cultured human dendritic cells is maintained by granulocyte/macrophage colony-stimulating factor plus interleukin 4 and downregulated by tumor necrosis factor α", J. Exp. Med. 179:1109-1118 (1994).
Schlom, In: Molecular foundations of Oncology, S. Broder, Ed., Mol. Fndns. Oncol., 105-107 (1991).
Schultes et al., "Immunotherapy of human ovarian carcinoma with OvaRex MAb-B43.13 in a human-PBL-SCID/BG mouse model", Hybridoma, 18(1):47-55 (1999) (abstract only).
Schwartz, "Cancer Markers," In: Cancer: Principles and Practice of Clinical Oncology, 41$^{th}$ Ed., 531-542 (1994).
Schwartzberg, "Clinical experience with edrecolomab: a monoclonal antibody therapy for colorectal carcinoma", Critical Reviews in Oncology/Hematology 40:17-24 (2001).
Semino et al., "Heterogeneity of the alpha-interferon-mediated overexpression of class-I and class-II major histocompatibility complex molecules in primary cultured cancer cells", J. Biol. Regs., 7:99-105 (1993).
Tassi et al., "Immunogenicity of anti-idiotypic antibodies and of their F(ab')2 fragments," Imm. Letts., 27:39-44 (1991).
Vrba et al., "Carcinoembryonic antigen: evidence for multiple antigenic determinants and isoantigens", PNAS, 72:4602-06 (1975).
Ward, "Unconjugated antibodies for cancer therapy: lessons from the clinic" Cancer Treatment Rev., 23:305-319 (1997).
Watts et al., "Suppressive Effect of Antibody on Processing of T Cell Epitopes", J. Exp. Med., 178:1459-1463 (1993).
Yin et al., "Serological and immunochemical analysis of Lewis y (Ley) blood group antigen expression in epithelial ovarian cancer," Int. J. Cancer, 65-406-412 (1996).
Mdiyalakan et al., Hybridoma 14:199-203 (1995).
Ghiron et al., Photochemistry and Photobiology 7:87-92 (1968).
Prodouz et al., Blood 70:589-392 (1987).
Jose et al., Molecular Immunology 24:1145-1150 (1987).
Kleckowski et al., Photochem. Photobiol. 1:299-304 (1962).
Murray et al., J.A.M.A. 8-14 (1955).
Kallenbach et al., Curr. Stud. Hematol. BloodTransfus. 70-82 (1989).
Sykes et al., The Journal of Neuclear Medicine 36:1913-1922 (1995).
Baum et al., Hybridoma 12:583-589 (1993).
Baum et al., Cancer 73:1121-1125 (1994).
Noujaim et al., Current Tumor Diagnosis 823-829 (1994).
Chatterjee et al., Cancer Immunol. Immunother. 38:75-82 (1994).
Thomson et al., Clin. Exp. Immunol. 98:351-357 (1994).
Kehoe, International Journal of Oncology 6:451-458 (1995).
Lanzavecchia, Science 260:937-944 (1993).
Wagner et al., Biotechnology Therapeutics 3:81-89 (1992).
Nemazee et al., PNAS 79:3828-3832 (1982).
Stevenson et al., Immunol 2:16-19 (1994).
Leoni et al., Int. J. Cancer 40:592-597 (1987).
Jose et al., Mol. Immunol. 24:1145-1150 (1987).
Imai et al., Acta Pathol., Japan 29:43-49 (1987).
Gura, Science 278:1041-1042 (1997).
Herbert et al., Dictionary of Immunology, Academic Press, London, pp. 58, 59, 72, 73, and 154 (1995).
Colman, P.M. "Structure of Antibody-Antigen Complexes: Implications for Immune Recognition", Advances in Immunology, 1998, 43: 99-132.
Golumbek et al., "The Antitumor Immune-Response as a Problem of Self-Nonself Discrimination—Implications for Immunotherapy", Immunologic Research, 1993, 12:183-192 (Abstract only).
Hilkens et al., "Is episialin/MUC1 involved in breast cancer progression?", Cancer Letters, 1995, 90: 27-33 (Abstract only).
Jacobs et al., "Clinical Use of Tumor Markers in Oncology", Current Problems in Cancer, 1991, pp. 299-350.
Lanzavecchia, A., "Mechanisms of antigen uptake for presentation", Current Opinion in Immunology, 1996, 8: 348-354.
Madiyalakan et al., "OVAREX™ MAb-B43.13:IFN-γ Could Improve the Ovarian Tumor Cell Sensitivity to CA125-Specific Allogenic Cytotoxic T Cells", Hybridoma, 1997, 16: 41-45.
Simitsek et al., "Modulation of Antigen Processing by Bound Antibodies Can Boost or Suppress Class II Major Histocompatibility Complex Presentation of Different T Cell Determinants", J. Experimental Medicine, 1995, 181: 1957-1963.

* cited by examiner

CHEMOTHERAPY/IMMUNOTHERAPY COMBINATIONS

OvaRex® MAb + Salvage Chemotherapy

| Chemo | Study No. | Patients treated | Responses to chemo | Immune Response |
|---|---|---|---|---|
| Carbo, Cis, Pac, Topo, Doxil, Gem, Doc, Cyt, Etop | 10 | 34 | Yes | Yes |
| Carbo, Topo, Gem, Etop | 08 | 7 | Yes | N.A. |
| Carbo, Cis, Pac, Doxil | 12 | 6 | Yes | Yes |

- Clinical experience in 3 studies
- More data emerging from Study 12 (20 patients treated)
- Encouraging clinical and immune responses especially CR & PRs with carboplatin and other agents in salvage setting

FIGURE 1

Patients can continue chemotherapy up to 6 cycles and OvaRex® up to 2 years.
Endpoints: Time to progression, QOL, Safety, Survival

AB2 RESPONSE AND RELATIONSHIP TO # OF INFUSIONS

Controlled Phase II (Study OVA-Gy-10)
Ab2 Response Vs. No. of Infusions

> 50% immune responders by week 9

Evidence for Drug Effect in Ab2 Responders: Disease characteristics of Ab2 responders vs non-responders

Study: OVA-Gy-10

|  | Ab2 ≥ 100 N (%) | Ab2 < 100 N (%) |
|---|---|---|
| FIGO IIIC or IV | 10 (71) | 11 (85) |
| TN(1)M or TNM(1) | 9 (53) | 1 (8) |
| Tumor Grade 3 | 12 (80) | 6 (46) |
| ECOG ≥ 1 | 6 (38) | 6 (46) |
| Malignant ascites | 8 (53) | 7 (58) |
| Staging lap residual > 1cm or not specified | 6 (38) | 6 (46) |
| Baseline CA125 ± SD | 188 ± 170 | *279 ± 281 |

*No statistical difference compared to placebo or to patients (pts) with Ab2 ≥ 100.

FIGURE 4

COMBINATION THERAPY FOR TREATING DISEASE

RELATED APPLICATIONS

This application is a continuation-in part of U.S. application Ser. No. 09/871,339, filed May 31, 2001, now abandoned which is a continuation of U.S. application Ser. No. 08/913,290, filed Mar. 20, 1998, now U.S. Pat. No. 6,241,985, which is a National Stage application of PCT application number PCT/IB96/00461, filed May 15, 1996; and is a continuation-in part of PCT application number PCT/IB02/05794, filed Oct. 28, 2002, which claims the benefit of U.S. provisional application 60/339,240, filed Oct. 26, 2001, each of which is hereby incorporated in its entirety by reference. PCT applications PCT/IB96/00461 and PCT/IB02/05794 were filed in English.

BACKGROUND OF THE INVENTION

1. Field of the Invention

The invention relates to immunology. More particularly the invention relates to the use of immunotherapy in combination with chemotherapy.

2. Summary of the Related Art

Despite the progress that modern medicine has made in treating cancer, cancer recurrence remains a concern. For a majority of cancers, typical treatment includes surgery followed by high doses of chemotherapy. A majority of these patients relapse and do not respond to other chemotherapeutic treatments. These patients then avail themselves to experimental or salvage treatments.

Current experimental regimens focus on mixing chemotherapies in an attempt to overcome resistance issues. Most of these treatments result in serious blood toxicities such as neutropenia, and thrombocytopenia. Other serious and frustrating symptoms to the patient include hair loss and nausea. Researchers are now looking at ways to enhance the immune system through less toxic means while still eliminating the cancer.

Many have turned to the use of chemotherapy in conjunction with antibody treatments. Many of these have also presented similar toxicities to the chemotherapy.

Thus, there remains a need to identify new treatments that not only treat the initial symptoms of a disease, but also alleviate and/or prevent recurrence of those symptoms.

SUMMARY OF THE INVENTION

In a first aspect the invention provides a method for treating cancer, comprising concurrently administering xenotypic monoclonal antibody and a chemotherapeutic drug to a patient suffering from cancer. Preferably the patient is human.

In a second aspect the invention provides a method for treating cancer, comprising surgical removal of the cancer, concurrent administration of a chemotherapeutic drug and a xenotypic monoclonal antibody in a dose equal to or less than 2 mg.

In a third aspect, the invention provides a method for treating cancer, comprising surgical removal of the cancer, administration of a xenotypic monoclonal antibody on weeks 1, 3, 5, 9, followed by concurrent administration of a chemotherapeutic drug and a xenotypic monoclonal antibody on week 12 in a dose equal to or less than 2 mg.

In a fourth aspect, the invention provides a method for inducing a host immune response in a patient against a multi-epitopic in vivo tumor antigen, which antigen does not elicit an effective host immune response, comprising concurrently administering to the patient a chemotherapeutic drug and a composition comprising a binding agent that specifically binds to a first epitope on the antigen and allowing the binding agent to form a binding agent/antigen pair, wherein a host immune response is elicited against a second epitope on the antigen.

In a fifth aspect, the invention provides a method for treating cancer, comprising concurrent administration of a chemotherapeutic drug, a binding agent, and an antigen.

In a sixth aspect, the invention provides a method for inducing a host immune response in a patient against a multi-epitopic in vivo tumor antigen, which antigen does not elicit an effective host immune response, comprising concurrently administering to the patient a chemotherapeutic drug and a composition comprising a binding agent present in an amount of from 0.1 µg to 2 mg per kg of body weight of the host, and wherein the binding agent specifically binds to an epitope on the antigen and an effective host immune response is elicited against a second epitope on the antigen.

In a seventh aspect, the invention provides a method for treating cancer, comprising administering a xenotypic antibody and a chemotherapeutic drug to a patient suffering from cancer.

BRIEF DESCRIPTION OF THE DRAWINGS

FIG. 1 provides a table illustrating the results of three clinical studies where Alt-2 is administered concurrently with a chemotherapeutic drug.

FIG. 4 is a table illustrating the different disease characteristics of Ab2 responders and Ab2 non-responders.

DETAILED DESCRIPTION

Figure 2:
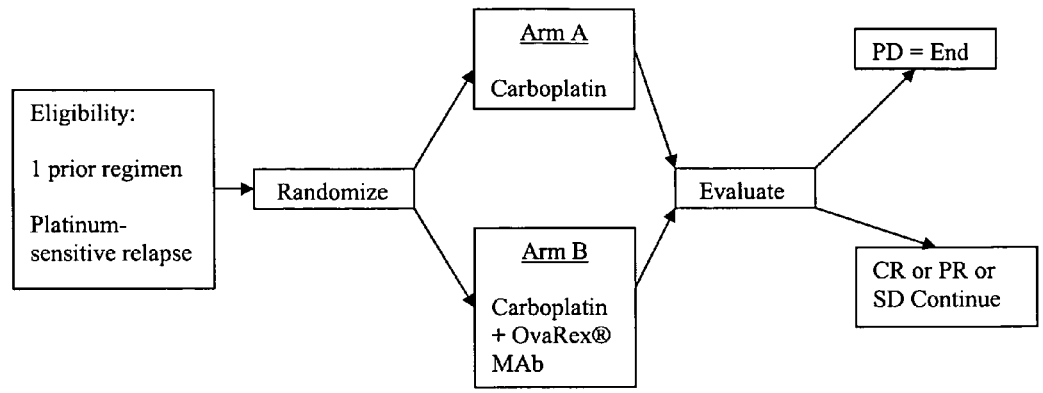
FIG. 2 is a diagram showing a non-limiting embodiment of the invention.
Figure 3:
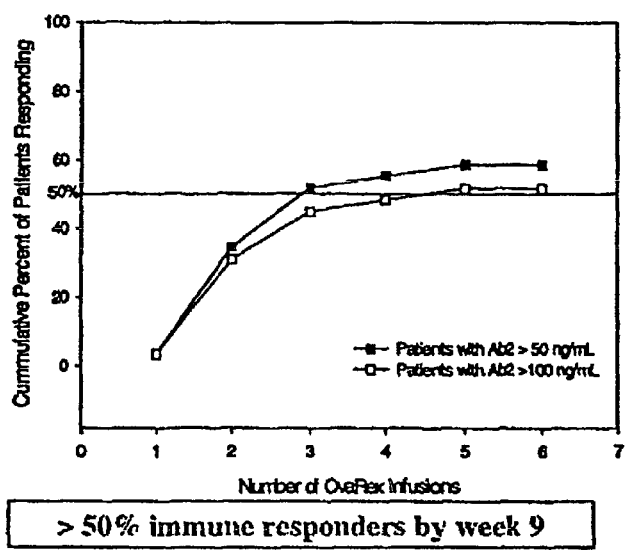
FIG. 3 is a graph showing the difference in the numbers between Ab2 responders (white squares) (effective immune response) and Ab2 non-responders (black squares) (ineffective immune response) over time.

The present invention stems from the discovery that a combination of immunotherapy with traditional chemotherapy and/or radiotherapy alleviates and/or prevents the recurrence of cancer. The presence of a host anti-xenotypic antibody response in a patient will stimulate an immune response. The inventors have exploited this discovery to develop therapeutics containing binding agents useful in immunotherapy and chemotherapeutic or radiotherapeutic drugs, as well as methods for using these therapeutics. The patents and publications cited herein reflect the level of skill in this field and are hereby incorporated by reference in their entirety to the same extent as if each was specifically and individually indicated to be incorporated by reference.

Accordingly in one embodiment, the invention provides a method for treating cancer, comprising concurrently administering xenotypic monoclonal antibody and a chemotherapeutic drug to a patient suffering from cancer. In some embodiments of the invention, the binding by the xenotypic monoclonal antibody of a first epitope exposes a second distinct epitope on the antigen. In some embodiments of the invention, the xenotypic monoclonal antibody, when bound to the antigen, forms an immunogenic complex. Exemplary xenotypic monoclonal antibodies ("MAb"), preferably include IgG1 antibodies; chimeric monoclonal antibodies ("C-MAb"); humanized antibodies; genetically engineered monoclonal antibodies ("G-MAb"); fragments of monoclonal antibodies (including but not limited to "F(Ab)₂", "F(Ab)" and "Dab"); and single chains representing the reactive portion of monoclonal antibodies ("SC-MAb"). The binding agent may be labeled or unlabeled.

Where the patient is human, preferred xenotypic monoclonal antibodies include, without limitation, murine monoclonal antibodies. Particularly preferred murine monoclonal antibodies include Alt-I (murine IgG1, specifically binds to MUC-1; ATCC No. PTA-975; American Type Culture Collection, Manassas, Va.), Alt-2 (OvaRex® MAb B43.13, murine IgG1, specifically binds to CA125; ATCC No. PTA-1883), Alt3 (murine IgG3, specifically binds to CA19.9; ATCC No. PTA-2691), Alt-4 (murine IgM, specifically binds to CA19.9; ATCC No. PTA-2692), Alt-5 (murine IgG1, specifically binds to CA19.9; ATCC No. PTA-2690); and Alt-6 (murine IgG1, specifically binds to prostate specific antigen (PSA); ATCC No. HB12526).

The mouse hybridoma AR20.5R8233, which produces the antibody Alt-1, was deposited with the American Type Culture Collection (ATCC), 10801 University Blvd., Manassas, VA 20110-2209, on Nov. 23, 1999, and was given ATCC deposit number PTA-975. The mouse hybridoma B43.13 (MCB-ALT1-96), which produces the antibody Alt-2/B43.13, was deposited with the American Type Culture Collection (ATCC), 10801 University Blvd., Manassas, VA 20110-2209, on May 18, 2000, and was given ATCC deposit number PTA-1883. The mouse hybridoma AR44.6 R1331, which produces the antibody Alt-3, was deposited with the American Type Culture Collection (ATCC), 10801 University Blvd., Manassas, VA 20110-2209, on Nov. 17, 2000, and was given ATCC deposit number PTA-2691. The mouse hybridoma AR18.4 R3313, which produces the antibody Alt-4, was deposited with the American Type Culture Collection (ATCC), 10801 University Blvd., Manassas, VA 20110-2209, on Nov. 17, 2000, and was given ATCC deposit number PTA-2692. The mouse hybridoma AR44.3 R15, which produces the antibody Alt-5, was deposited with the American Type Culture Collection (ATCC), 10801 University Blvd., Manassas, VA 20110-2209, on Nov. 17, 2000, and was given ATCC deposit number PTA-2690. The mouse hybridoma AR47.47, which produces the antibody Alt-6/AR47.47, was deposited with the American Type Culture Collection (ATCC), 10801 University Blvd., Manassas, VA 20110-2209, on Apr. 29, 1998, and was given ATCC deposit number HB-12526.

In certain embodiments of the invention, the chemotherapeutic drug used is commercially available. Some non limiting examples include carboplatin, cisplatin, docetaxel, paclitaxel, doxorubicin, HCl liposome injection, topotecan, hydrochloride, gemcitabine, cyclophosphamide, and etoposide or any combination thereof.

In preferred embodiments the chemotherapeutic drug is administered within a week before or after the murine monoclonal antibody.

Chemotherapeutic agents of the invention include chemotherapeutic drugs commercially available. Merely to illustrate, the chemotherapeutic can be an inhibitor of chromatin function, a topoisomerase inhibitor, a microtubule inhibiting drug, a DNA damaging agent, an antimetabolite (such as folate antagonists, pyrimidine analogs, purine analogs, and sugar-modified analogs), a DNA synthesis inhibitor, a DNA interactive agent (such as an intercalating agent), and/or a DNA repair inhibitor.

Chemotherapeutic agents may be categorized by their mechanism of action into, for example, the following groups: anti-metabolites/anti-cancer agents, such as pyrimidine analogs (5-fluorouracil, floxuridine, capecitabine, gemcitabine and cytarabine) and purine analogs, folate antagonists and related inhibitors (mercaptopurine, thioguanine, pentostatin and 2-chlorodeoxyadenosine (cladribine)); antiproliferative/antimitotic agents including natural products such as vinca alkaloids (vinblastine, vincristine, and vinorelbine), microtubule disruptors such as taxane (paclitaxel, docetaxel), vincristin, vinblastin, nocodazole, epothilones and navelbine, epidipodophyllotoxins (etoposide, teniposide), DNA damaging agents (actinomycin, amsacrine, anthracyclines, bleomycin, busulfan, camptothecin, carboplatin, chlorambucil, cisplatin, cyclophosphamide, cytoxan, dactinomycin, daunorubicin, doxorubicin, epirubicin, hexamethylmelamineoxaliplatin, iphosphamide, melphalan, merchlorehtamine, mitomycin, mitoxantrone, nitrosourea, plicamycin, procarbazine, taxol, taxotere, teniposide, triethylenethiophosphoramide and etoposide (VP16)); antibiotics such as dactinomycin (actinomycin D), daunorubicin, doxorubicin (adriamycin), idarubicin, anthracyclines, mitoxantrone, bleomycins, plicamycin (mithramycin) and mitomycin; enzymes (L-asparaginase which systemically metabolizes L-asparagine and deprives cells which do not have the capacity to synthesize their own asparagine); antiplatelet agents; antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nitrosoureas (carmustine (BCNU) and analogs, streptozocin), trazenes-dacarbazinine (DTIC); antiproliferative/antimitotic antimetabolites such as folic acid analogs (methotrexate); platinum coordination complexes (cisplatin, carboplatin), procarbazine, hydroxyurea, mitotane, aminoglutethimide; hormones, hormone analogs (estrogen, tamoxifen, goserelin, bicalutamide, nilutamide) and aromatase inhibitors (letrozole, anastrozole); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory agents; antisecretory agents (breveldin); immunosuppressives (cyclosporine, tacrolimus (FK-506), sirolimus (rapamycin), azathioprine, mycophenolate mofetil); anti-angiogenic compounds (TNP-470, genistein) and growth factor inhibitors (vascular endothelial growth factor (VEGF) inhibitors, fibroblast growth factor (FGF) inhibitors); angiotensin receptor blocker; nitric oxide donors; anti-sense oligonucleotides; antibodies (trastuzumab, rituximab); cell cycle inhibitors and differentiation inducers (tretinoin); mTOR inhibitors, topoisomerase inhibitors (doxorubicin (adriamycin), amsacrine, camptothecin, daunorubicin, dactinomycin, eniposide, epirubicin, etoposide, idarubicin, irinotecan (CPT-11) and mitoxantrone, topotecan, irinotecan), corticosteroids (cortisone, dexamethasone, hydrocortisone, methylpednisolone, prednisone, and prenisolone); growth factor signal transduction kinase inhibitors; mitochondrial dysfunction inducers, toxins such as Cholera toxin, ricin, *Pseudomonas* exotoxin, *Bordetella pertussis* adenylate cyclase toxin, or diphtheria toxin, and caspase activators; and chromatin disruptors. Preferred dosages of the chemotherapeutic agents are consistent with currently prescribed dosages.

The methods according to the invention are useful for providing a therapeutic benefit to patients suffering from cancer. As used herein, the term "cancer" is used to mean a condition in which a cell in a patient's body undergoes abnormal, uncontrolled proliferation. The abnormal cell may proliferate to form a solid tumor, or may proliferate to form a multitude of cells (e.g., leukemia). Note that because cancer is the abnormal, uncontrolled proliferation of a patient's cell, the term does not encompass the normal proliferation of a cell, such as a stem cell or a spermatocyte.

By "treating a patient suffering from cancer" is meant that the patient's symptoms are alleviated following treatment according to the invention. In one non-limiting example, a patient suffering from a highly metastatic cancer (e.g., breast cancer) is treated where additional metastasis either do not occur, or are reduced in number as compared to a patient who does not receive treatment. In another non-limiting example, a patient is treated where the patient's solid cancer either becomes reduced in size or does not increase in size as compared to a patient who does not receive treatment. In yet another non-limiting example, the number of cancer cells (e.g., leukemia cells) in a treated patient either does not increase or is reduced as compared to the number of cancer cells in a patient who does not receive treatment. In preferred embodiments the patient is human.

It will be appreciated that a "patient suffering from cancer" of the invention may express the mutant protein and not yet be symptomatic for the disease. For example, where the cancer is colon cancer (which is associated with the mutant K-ras protein), a patient with a mutant K-ras protein in some cells of the colon is a patient according to the invention even though that patient may not yet be symptomatic for colon cancer. "Associated with a mutant protein" means signs or symptoms of illness in a majority of patients are present when the mutant protein is present in the patient's body, but in which signs or symptoms of illness are absent when the mutant protein is absent from the patient's body. "Signs or symptoms of illness" are clinically recognized manifestations or indications of disease.

In one embodiment of the present invention, the patient in need of treatment is suffering from cancer of the prostate, ovaries, breast, stomach, lung, colon, and skin. In a preferred embodiment, the patient in need of treatment is a human.

Preferably, the therapeutic compositions of the invention further comprise a pharmaceutically acceptable carrier. By "pharmaceutically acceptable carrier" is meant a carrier that is physiologically acceptable to the administered patient. One exemplary pharmaceutically acceptable carrier is physiological saline. Other pharmaceutically-acceptable carriers and their formulations are well-known and generally described in, for example, *Remington's Pharmaceutical Sciences* (18$^{th}$ Edition, ed. A. Gennaro, Mack Publishing Co., Easton, Pa., 1990).

"Administering" as used herein means providing the composition to the patient in a manner that results in the composition being inside the patient's body. Such an administration can be by any route including, without limitation, parenteral, sub-cutaneous, intradermal, intravenous, intra-arterial, intra-peritoneal, and intramuscular.

Regardless of the route of administration selected, the compounds of the present invention, which may be used in a suitable hydrated form, and/or the pharmaceutical compositions of the present invention, are formulated into pharmaceutically acceptable dosage forms such as described below or by other conventional methods known to those of skill in the art.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular composition employed, the age, sex, weight, condition, general health and prior medical history of the patient being treated, and like factors well known in the medical arts.

In a second aspect the invention provides a method for treating cancer, comprising surgery, administration of a chemotherapeutic drug, administration of a xenotypic monoclonal antibody in a dose equal to or less than 2 mg given by intravenous infusion over 20 minutes during weeks 1, 3, 5, 9, then every 8 weeks, followed by administration of a chemotherapeutic drug within 5 days of the administration of the binding agent.

In certain, non-limiting embodiments of the invention, the xenotypic antibody, e.g., Alt-2, is administered as a 2 mg dose dissolved in 50 mL saline and infused slowly preferably over approximately 20 minutes. If an allergic or other reaction occurs that may limit the completion of the dose, then a lower dose may be employed at that time or with subsequent treatments, so that the expected dose range would be 1-2 mg per treatment. Premedication with oral or intravenous dyphenhydramine (25 to 50 mg) is usually administered to lessen the risk of allergic reaction to the protein. The schedule used for combined Alt-2 and chemotherapy comprises administering Alt-2 at the dose above at weeks 1, 3, 5, 7, 9 with chemotherapy administered with Alt-2 on weeks 12 through 26. Administration of Alt-2 may be started after recovery from any required surgery that is done prior to the chemotherapy and then continued up to, and during, the chemotherapy treatment period. The chemotherapy can be given in 3-4 week cycles or other schedules according to the treating physician and common clinical practice. Chemotherapy may continue for up to six cycles followed by the xenotypic antibody administration every twelve weeks for up to two years.

In another aspect, the method provides for treating cancer comprising surgery, followed within seven days by administration of a xenotypic monoclonal antibody in a dose equal to or less than 2 mg given by intravenous infusion over 20 minutes during weeks 1, 3, 5, 9, then every 8 weeks with concurrent administration of a chemotherapeutic drug at week 3 and thereafter.

In another aspect of the invention, the murine antibody is administered at week 1 after completing standard surgery but has not yet begun chemotherapy. The murine antibody is administered in a dose equal to or less than 2 mg via a 20 minute intravenous infusion followed by a second treatment and concurrent administration of a chemotherapeutic drug on weeks 6 and beyond. "Concurrent Administration" means administration within a relatively short time period from each other. Preferably such time period is less than 2 weeks, more preferably less than 7 days, most preferably less than 1 day and could even be administered simultaneously.

The expected progression-free survival times may be measured in months to years, depending on prognostic factors including the number of relapses, stage of disease, and other factors. Overall survival is also measured in months to years. In the case of ovarian cancer, the addition of the xenotypic monoclonal antibody, Alt-2 is expected to increase the time to recurrence or progression, and may also prolong the survival time. Any improvement of 2 months or longer is usually considered to be clinically meaningful.

In one aspect, the invention provides a method for inducing a host immune response in a patient against a multi-epitopic in vivo tumor antigen in present in the host's serum, which antigen does not elicit a host immune response, comprising administering to the patient a chemotherapeutic drug and a composition comprising a binding agent that specifically binds to a first epitope ton the antigen and allowing the binding agent to form a binding agent/antigen pair, wherein a host immune response is elicited against a second epitope on the antigen. Exemplary multi-epitopic antigens are described in and herein incorporated by reference in Nicodemus C. F. et al, Expert Rev. *Vaccines* 1(1): 34-48 (2002); Qi et al, *Hybridoma and Hybridomics* 20: 313-323 (2001); and Berlyn et al., *Clin. Immunol.* 101: 276-283, (2001).

A "binding agent", as used herein, refers to one member of a binding pair, including an immunologic pair, e.g., a binding moiety that is capable of binding to an antigen, preferably a single epitope expressed on the antigen, such as a predetermined tumor antigen. In some embodiments of the invention, the binding of a first single epitope exposes a second distinct epitope on the antigen. In one embodiment of the invention, the binding agent, when bound to the antigen, forms an immunogenic complex. Exemplary binding agents include, but are not limited to: antibodies, monoclonal antibodies ("MAb"), preferably IgG1 antibodies; chimeric monoclonal antibodies ("C-MAb"); humanized antibodies; genetically engineered monoclonal antibodies ("G-MAb"); fragments of monoclonal antibodies (including but not limited to "F(Ab)$_2$", "F(Ab)" and "Dab"); single chains representing the reactive portion of monoclonal antibodies ("SC-MAb"); antigen-binding peptides; tumor-binding peptides; a protein, including receptor proteins; peptide; polypeptide; glycoprotein; lipoprotein, or the like, e.g., growth factors; lymphokines and cytokines; enzymes, immune modulators; hormones, for example, somatostatin; any of the above joined to a molecule that mediates an effector function; and mimics or fragments of any of the above. The binding agent may be labeled or unlabeled.

Preferred binding agents of the invention are monoclonal antibodies. Where the patient is human, these xenotypic monoclonal antibodies include, without limitation, murine monoclonal antibodies. Particularly preferred murine monoclonal antibodies include Alt-1 (murine IgG1, specifically binds to MUC-1; ATCC No. PTA-975; American Type Culture Collection, Manassas, VA), Alt-2(OvaRex® MAb B43.13, murine IgG1, specifically binds to CA125; ATCC No. PTA-1883), Alt3(murine IgG3, specifically binds to CA19.9; ATCC No. PTA-2691), Alt-4(murine IgM, specifically binds to CA19.9; ATCC No. PTA-2692), Alt-5(murine IgG1, specifically binds to CA19.9; ATCC No. PTA-2690); and Alt-6(murine IgG1, specifically binds to prostate specific antigen (PSA); ATCC No. HB-12526).

A "multi-epitopic in vivo tumor antigen" is an antigen that present multiple epitopes on its surface. Some non-limiting examples of such antigens include CA 125, MUC-1, PSA, CA19.9, and TAG-72.

"Inducing a host immune response" means that the patient experiences alleviation or reduction of signs or symptoms of illness, and specifically includes, without limitation, prolongation of survival. In certain preferred embodiments of the methods according to the invention, a CD8+ IFN-γ producing T cell is activated to induce a cytotoxic T lymphocyte (CTL) immune response in the patient administered the murine monoclonal antibody. In certain embodiments of the methods according to the invention, a CD4+ IFN-γ producing T cell is activated to induce a helper T cell immune response in the patient administered with the composition. These activated CD4+ IFN-γ producing T cells (i.e., helper T cells) provide necessary immunological help (e.g. by release of cytokines) to induce and maintain not only CTL, but also a humoral immune response mediated by B cells. Thus, in certain embodiments of the methods according to the invention, a humoral response to the antigen is activated in the patient administered with the composition.

Activation of a CD8+ and/or CD4+ IFN-γ, producing T cells means causing T cells that have the ability to produce IFN-γ to actually produce IFN-γ, or to increase their production of IFN-γ. "Induction of CTL" means causing potentially cytotoxic T lymphocytes to exhibit antigen specific cytotoxicity. "Antigen specific cytotoxicity" means cytotoxicity against a cell presenting an antigen that is associated with the antigen associated with the cancer that is greater than an antigen that is not associated with the cancer. "Cytotoxicity" refers to the ability of the cytotoxic T lymphocyte to kill the target cell. Preferably, such antigen-specific cytotoxicity is at least 3-fold, more preferably 10-fold greater, more preferably more than 100-fold greater than cytotoxicity against a cell not presenting the antigen not associated with the cancer.

In another aspect, the invention includes a method for treating cancer, comprising concurrent administration of a chemotherapeutic drug, a binding agent, and an antigen.

In a further aspect, the invention provides a method for inducing a host immune response in a patient against a multi-epitopic in vivo tumor antigen, which antigen does not elicit an effective host immune response, comprising concurrently administering to the patient a chemotherapeutic drug and a composition comprising a binding agent present in an amount of from 0.1 μg to 2 mg per kg of body weight of the host, and wherein the binding agent specifically binds to an epitope on the antigen and an effective host immune response is elicited against a second epitope on the antigen.

Equivalents

Those skilled in the art will recognize, or be able to ascertain using no more than routine experimentation, many equivalents to the specific embodiments of the invention described herein. Such equivalents are intended to be encompassed by the following claims.

All of the above-cited references and publications are hereby incorporated by reference in their entireties.

The following example is intended to further illustrate certain particularly preferred embodiments of the invention and is not intended to limit the scope of the invention.

EXAMPLE I

Clinical and Immunologic Outcomes of Patients with Recurrent Epithelial Ovarian Cancer (EOC) Treated with B43.13 and Chemotherapy (Ct)-Interim Immunology and Clinical Results from Study OVA-Gy-12

Patients with recurrence after platinum therapy and a first surgery and were enrolled if they were candidates for secondary surgery and continued chemotherapy. Alt-2 was administered by 20-minute infusion in weeks 1, 3, 5, and 9 prior to initiation of chemotherapy, and then an option to continue every 8 weeks×2 doses concurrent with chemotherapy on weeks 12 and 26. Humoral immune responses, including HAMA, Ab2 and anti-CA 125 antibody, were assessed at baseline and serially. Using gamma-interferon ELISPOT assay, T cell responses were evaluated for activation by Alt-2, CA125, or autologous tumor.

20 patients were enrolled; median follow-up was 6 months ranging up to 2 years. Alt-2 was well tolerated and did not produce drug-related serious adverse reactions. In 14 of 19 (710/6) evaluable patients, robust treatment-emergent humoral responses were observed to the constant (HAMA) and variable region of the antibody (Ab2). To date, 5 of 8 (62.5%) patients tested demonstrated functionally active T cells, stimulated by CAI 25 or by autologous tumor. T cell responses to Alt-2 were demonstrated in 4 patients. T cell responses were MHC class 1 and 11 restricted, indicating the activation of CTL (cytotoxic T lymphocytes) and T helper cells. Immune responses were commonly induced by wk 12 after 4 doses, and were generally maintained in patients continuing combined treatment with Alt-2 and chemotherapy. 75% are still alive and median survival has not been reached at 120 weeks.

Conclusions: Alt-2 is well tolerated and induces multiple antigen-specific immune responses, even when combined with chemotherapy. In advanced EOC, these data are among the first to demonstrate induction of tumor-specific T cells.

We claim:

1. A method for treating cancer, comprising administering to a patient suffering from cancer a chemotherapeutic drug, and a composition comprising an unlabeled xenotypic monoclonal antibody specific for a multi-epitopic in vivo antigen present in the patient's serum, wherein the multi-epitopic in vivo antigen is MUC-1, CA 1251, prostate specific antigen, CA 19.9, or TAG-72, wherein the chemotherapeutic drug is administered within a week of administering the composition.

2. The method of claim 1, wherein the xenotypic monoclonal antibody is murine.

3. The method of claim 2, wherein the xenotypic monoclonal antibody is selected from the group consisting of: Alt-1 which is producible by a hybridoma having ATCC deposit number PTA-975, Alt-2 which is producible by a hybridoma having ATCC deposit number PTA-1883, Alt-3 which is producible by a hybridoma having ATCC deposit number PTA-2691, Alt-4 which is producible by a hybridoma having ATCC deposit number PTA-2692, Alt-5 which is producible by a hybridoma having ATCC deposit number PTA-2690, and Alt-6 which is producible by a hybridoma having ATCC deposit number HB 12526.

4. The method of claim 1, wherein the patient is a human.

5. The method of claim 1 or 3, wherein the xenotypic monoclonal antibody in the composition is administered in a dose of less than or equal to 2 mg.

6. The method of claim 2, further comprising surgically removing the cancer.

7. A method for treating cancer, comprising:
(1) surgically removing the cancer, and
(2) administering:
    (a) a composition comprising an unlabeled xenotypic monoclonal antibody specific for a multi-epitopic in vivo antigen present in the patient's serum, said xenotypic monoclonal antibody is in a dose equal to or less than 2 mg, and,
    (b) a chemotherapeutic drug,
    wherein the chemotherapeutic drug is administered within a week of administering the composition.

8. The method of claim 7, wherein the xenotypic monoclonal antibody is selected from the group consisting of: Alt-1 which is producible by a hybridoma having ATCC deposit number PTA-975, Alt-2 which is producible by a hybridoma having ATCC deposit number PTA-1883, Alt-3 which is producible by a hybridoma having ATCC deposit number PTA-2691, Alt-4 which is producible by a hybridoma having ATCC deposit number PTA-2692, Alt-5 which is producible by a hybridoma having ATCC deposit number PTA-2690, and Alt-6 which is producible by a hybridoma having ATCC deposit number HB 12526.

9. The method of claim 7, wherein administration of the composition comprises a 20 minute intravenous infusion.

10. A method for treating cancer in a patient, comprising:
(1) surgically removing the cancer, and
(2) administering a composition comprising an unlabeled xenotypic monoclonal antibody at weeks 1, 3, 5, 7 and 9, followed by concurrently administering a chemotherapeutic drug and the composition, said xenotypic monoclonal antibody in the composition is administered in a dose less than or equal to 2 mg at week 12.

11. The method of claim 9, wherein the xenotypic monoclonal antibody is selected from the group consisting of: Alt-1 which is producible by a hybridoma having ATCC deposit number PTA-975, Alt-2 which is producible by a hybridoma having ATCC deposit number PTA-1883, Alt-3 which is producible by a hybridoma having ATCC deposit number PTA-2691, Alt-4 which is producible by a hybridoma having ATCC deposit number PTA-2692, Alt-5 which is producible by a hybridoma having ATCC deposit number PTA-2690, and Alt-6 which is producible by a hybridoma having ATCC deposit number HB 12526.

12. A method for inducing a host immune response in a patient against a multi-epitopic in vivo tumor antigen comprising administering to the patient a chemotherapeutic drug and a composition comprising an unlabeled monoclonal antibody or a fragment thereof that specifically binds to a first epitope on the antigen and allowing the monoclonal antibody or fragment thereof to form a monoclonal antibody or fragment thereof / antigen pair, wherein a host immune response is elicited against a second epitope on the antigen, wherein antigen is selected from the group consisting of MUC-1, CA 125, prostate specific antigen, CA 19.9 or TAG-72, wherein said antigen does not elicit an effective host immune response, wherein the chemotherapeutic drug is administered within a week of administering the monoclonal antibody and wherein the monoclonal antibody is selected from the group consisting of: Alt-1 which is producible by a hybridoma having ATCC deposit number PTA-975, Alt-2 which is producible by a hybridoma having ATCC deposit number PTA-1883, Alt-3 which is producible by a hybridoma having ATCC deposit number PTA-2691, Alt-4 which is producible by a hybridoma having ATCC deposit number PTA-2692, Alt-5 which is producible by a hybridoma having ATCC deposit number PTA-2690, and Alt-6 which is producible by a hybridoma having ATCC deposit number RB 12526.

13. The method of claim 12, wherein the monoclonal antibody is a murine xenotypic monoclonal antibody.

14. The method of claim 12, wherein the patient is human.

15. The method of claim 12, wherein the antibody is administered in a dose of equal to or less than 2 mg.

16. The method of claim 12, further comprising surgically removing the cancer.

17. A method for treating cancer, comprising administering a chemotherapeutic drug, an antigen, and a monoclonal antibody or a fragment thereof that binds the antigen, wherein the chemotherapeutic drug is administered within a week of administering the monoclonal antibody and wherein the monoclonal antibody is selected from the group consisting of: Alt-1 which is producible by a hybridoma having ATCC deposit number PTA-975, Alt-2 which is producible by a hybridoma having ATCC deposit number PTA-1883, Alt-3 which is producible by a hybridoma having ATCC deposit number PTA-2691, Alt-4 which is producible by a hybridoma having ATCC deposit number PTA-2692, Alt-5 which is producible by a hybridoma having ATCC deposit number PTA-2690, and Alt-6 which is producible by a hybridoma having ATCC deposit number HB 12526.

18. The method of claim 17, wherein the patient is human.

19. The method of claim 17, wherein the antibody is administered in a dose of equal to or less than 2 mg.

20. The method of claim 17, wherein the monoclonal antibody is a murine monoclonal antibody.

* * * * *